(12) United States Patent  (10) Patent No.: US 6,690,280 B2
Citrenbaum et al.  (45) Date of Patent: Feb. 10, 2004

(54) APPARATUS AND PROCESS FOR INFUSION MONITORING

(75) Inventors: Richard A. Citrenbaum, 395 Mt. Tom Rd., Bishop, CA (US) 93514; Laurence R. Nicholson, Nevada City, CA (US); Clifford A. Tyner, Grass Valley, CA (US)

(73) Assignee: Richard A. Citrenbaum, Bishop, CA (US)

( * ) Notice: Subject to any disclaimer, the term of this patent is extended or adjusted under 35 U.S.C. 154(b) by 101 days.

(21) Appl. No.: 09/948,446

(22) Filed: Sep. 7, 2001

(65) Prior Publication Data

US 2003/0048185 A1 Mar. 13, 2003

(51) Int. Cl.[7] .............................................. G08B 21/00
(52) U.S. Cl. ................. 340/603; 340/612; 128/DIG. 13
(58) Field of Search ................................. 340/603, 612, 340/613, 618; 604/245, 246; 128/DIG. 13

(56) References Cited

U.S. PATENT DOCUMENTS

| | | | |
|---|---|---|---|
| 2,706,755 A | | 4/1955 | Krasno |
| 3,287,721 A | | 11/1966 | Baehr |
| 3,389,387 A | | 6/1968 | Hulse et al. |
| 3,390,238 A | | 6/1968 | O'Neill |
| 4,137,915 A | * | 2/1979 | Kamen ........................ 604/65 |
| 4,176,349 A | | 11/1979 | Fliegel |
| 4,198,626 A | | 4/1980 | Rauscher |
| 4,650,464 A | | 3/1987 | Ruiz et al. |
| 4,756,706 A | * | 7/1988 | Kerns et al. ................... 604/66 |
| 4,794,379 A | * | 12/1988 | Wang .......................... 340/624 |
| 4,931,777 A | | 6/1990 | Chiang |
| 5,003,296 A | * | 3/1991 | Lee ............................. 340/618 |
| 5,012,227 A | * | 4/1991 | Jung ........................... 340/618 |
| 5,098,409 A | | 3/1992 | Stock |
| 5,112,319 A | | 5/1992 | Lai |
| 5,121,107 A | | 6/1992 | Newell |
| 6,121,555 A | | 9/2000 | Nowosielski et al. |

* cited by examiner

*Primary Examiner*—John Tweel
(74) *Attorney, Agent, or Firm*—Kelly Bauersfeld Lowry & Kelley, LLP (57) ABSTRACT

A process for monitoring infusion into a patient includes hanging a fluid bag from a monitoring apparatus. The weight of the fluid bag is periodically measured, using an electronic weight sensing mechanism and a microprocessor, to detect either a no-fluid-flow condition, a near empty bag condition, or a preselected amount of fluid loss condition. A switch is depressed on the monitoring apparatus for selecting the monitoring of an amount of fluid to be infused totaling less than the fluid within the fluid infusion bag. Otherwise, the apparatus detects a near empty bag condition. An alarm is activated when either the no-fluid-flow condition, the near empty bag condition, or the preselected amount of fluid loss condition has been detected. The rate of fluid loss from the fluid bag can be calculated and displayed.

26 Claims, 9 Drawing Sheets

APPARATUS AND PROCESS FOR INFUSION MONITORING

BACKGROUND OF THE INVENTION

The present invention relates generally to the field of infusion monitoring and alarm devices. More particularly, the present invention relates to an infusion monitoring apparatus which enables a healthcare provider to be alerted when a predetermined amount of fluid has been infused, or the infusion bag is nearly empty.

Intravenous supply and irrigation systems are widely used in medical treatments to supply and dispense fluids, such as sterile water, nutrients, medicines, saline, blood or blood products, etc. A conventional way to dispense an intravenous fluid is to suspend a supply of the fluid in a bag or bottle above the patient, connect the length of tubing to an outlet of the fluid supply, and deliver the fluid to the patient via the tubing through a needle inserted into the patient. By suspending the fluid supply above the patient, the fluid can be delivered to the patient at a desired pressure.

In some cases, the delivery of such fluids in this manner occurs over a period of several hours. In other instances, the rate of fluid delivery is much quicker. In some situations, it is desired to monitor the delivery of the fluid so that the delivery of the fluid can be stopped before the fluid runs low or so that a new supply of fluid can be provided to maintain an uninterrupted flow to the patient. In other situations, less than a full amount of the fluid supply is desired to be infused.

If a fluid being delivered runs low or even runs out before a nurse or other medical attendant detects the condition, the patient may experience undesirable effects. These undesirable effects can include clotting of the infusion line, introduction of air into the infusion line, improper infusion volume, and so forth. Running out of surgical irrigation fluid can impair visualization of the surgical field and delay surgery while the fluid bag is replaced and air is evacuated from the line.

It is often necessary in the administration of intravenous to a patient to know exactly how much fluid a particular patient has received over a given period of time. The amount and rate of fluid infused into the patient along with monitored changes in the patient's condition can determine if additional infusions are indicated and how rapidly the fluids should be infused.

Devices which monitor the infusion of intravenous and irrigation solutions and provide a warning when such infusion has reached a predetermined extent are well known in the art. One group of devices makes use of a scale mechanism, such as a see-saw. When the amount of remaining fluid falls below some predetermined value, the see-saw tilts and actuates an electrical switch to trigger an alarm. Although the scale-based devices are simple, the springs used in the scales are quite sensitive to jolts or shocks that can occur, for example, if the patient accidentally strikes the device.

Another type of prior art device makes the use of a clip or clamp together with elements that complete an electrical signal circuit as the reservoir bag collapses on emptying. However, the clamp can effect the rate of flow of the IV fluid and the alerting signal is only activated when the reservoir is empty.

Many other devices utilize some form of spring extension which provides, in affect, a weighing of the slowly decreasing supply of fluid. In these devices a switch means is provided which actuates a warning signal when the weight of the fluid being administered has reached the desired level. These devices also experience sensitivity to jolts or shocks and can false alarm. Although these devices may initially provide accurate signaling capability, their inherent design principle of weight sensing by spring extension has failed to provide the requisite long-term accuracy. This failure is due to the ever-increasing fatigue of the spring caused by its repeated extension. Over a period of time this fatigue results in a change in the spring constant as the degree of fatigue increases.

Still other prior art devices use optical sensing equipment to sense the fluid level of the dripper and to monitor the fluid delivery system for occlusion or bubbles in the fluid. However, these devices have been found to be extremely complex and expensive. All known devices either monitor infusion rate or fluid empty condition.

Accordingly, there is a need for an infusion monitoring apparatus which can be used to monitor various infusion end-points, including monitoring predetermined infusion volumes and detecting almost empty infusion bags. Such an apparatus should also be able to detect very low or no flow conditions. Such an apparatus should not be sensitive to bumps or jolts, and should remain accurate over time. Such an apparatus should be easy to install and use by medical attendants. Moreover, such a device should be capable of being set to differing amounts of fluid infusion, and preferably calculate the rate of such infusion. The present invention fulfills these needs and provides other related advantages.

SUMMARY OF THE INVENTION

The present invention resides in an infusion monitoring apparatus which overcomes the shortcomings described above. The apparatus can be used as a monitor for any infusion where the bag is hanging, including gravity and infusion pump methods. The apparatus is particularly adapted for use in the gravity infusion environment.

The apparatus is comprised of a pole clamp extending from a housing and configured for removable attachment to a pole. An arm extends from the housing and has an end configured for holding an infusion fluid bag. Typically, the arm extends horizontally from the housing, generally opposite the pole clamp. An electronic weight sensing mechanism is disposed within the housing and associated with the arm. In a particularly preferred embodiment, the mechanism comprises a pair of magnets associated with the arm, and a Hall-effect sensor disposed within a gap between the magnets. Alternatively, the weight sensing mechanism comprises a load-cell associated with the arm. A control circuit, typically including a microprocessor, is electronically connected to the sensing mechanism for detecting a no-fluid-flow condition, a near empty bag condition, or a preselected amount of fluid loss condition. The apparatus is configured to always detect when a no-fluid-flow condition is present. The user may select to monitor and detect a pre-selected amount of fluid loss, such as 250 ml or 500 ml, otherwise, the apparatus monitors the infusion to detect and alarm when near-empty infusion condition occurs. Ideally, the infusion rate is monitored and displayed as well. The monitoring apparatus includes an alarm which is activated when the no-fluid-flow condition, the near empty bag condition, or the preselected amount of fluid loss condition has been detected. Preferably, the apparatus also includes a low battery alarm, for indicating battery replacement.

The process for monitoring gravity infusion into a patient generally comprises the steps of first hanging a fluid bag from the monitoring apparatus. The weight of the fluid bag is periodically measured, using the electronic weight sensing mechanism and the control circuit, to detect the no-fluid-flow condition, the near empty bag condition, or the preselected amount of fluid loss condition. An alarm is activated when any of these conditions are detected.

A near empty bag set point is set by hanging a weight from the monitor and apparatus and electronically saving the near empty bag set point weight. Typically, the near empty bag set point weight approximates an empty fluid infusion bag system, having a nominal amount of fluid therein. However, detection of the near empty condition is programmable to accommodate a range of infusion bags and setups as well as user preference. Users may wish to program the apparatus so that the near empty alarm is activated when the infusion bag has only 10–20 ml of remaining fluid, while others may wish to program the apparatus to alarm when there is an excess of 100 ml remaining in the infusion bag. Alternatively, a switch on the monitoring apparatus is depressed for selecting the monitoring of an amount of fluid to be infused totaling less than the fluid capacity of the fluid bag. For example, a 500 ml button can be depressed to select the monitoring of 500 ml of fluid to be infused.

Preferably, measuring includes the steps of taking multiple weight measurements over a short period of time and creating a reading, typically a linear-sloped reading, which is electronically saved. If the reading is within acceptable limits when compared to prior electronically saved readings, the reading is accepted. However, if it is determined that the reading is not within acceptable limits, additional weight measurements are taken over a short period of time to create a new reading if the immediately prior reading was without the acceptable limits.

The monitoring apparatus can be programmed such that an alarm is activated if no fluid loss is detected over a period of time. The monitoring apparatus can also be programmed to calculate and display the rate of fluid loss from the fluid bag.

In order to conserve power, the monitoring apparatus is maintained in a semi-inactive, battery conserving state and periodically self-activated to determine if a weight has been hung from the monitoring apparatus. Hanging a weight from the monitoring apparatus automatically activates the apparatus to its full operation.

The invention anticipates the use of a central station which monitors more than one monitoring apparatus. In such instance, a signal is transmitted from a monitoring apparatus to a remote electronic device to activate the alarm when the no-fluid-flow condition, the near empty bag condition, or the preselected amount of fluid loss condition has been detected.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

As shown in the drawings for purposes of illustration, the present invention is concerned with an infusion monitoring apparatus, generally illustrated in FIGS. 1–4 and referred to by the reference number 10. The apparatus 10 is intended for use in any medical setting wherein an infusion bag 12 having fluid 14 is to be infused into a patient. The apparatus 10 monitors the weight of the fluid bag 12 and sounds an audible alarm when the weight is near the empty weight, or a preselected amount of fluid has been dispensed from the bag 12. This will allow the healthcare staff to change the fluid bag 12 before it is completely empty and the fluid lines 16 fill with air, or adjust the rate of flow of the fluid 14, or cease fluid infusion.

Figure 1:
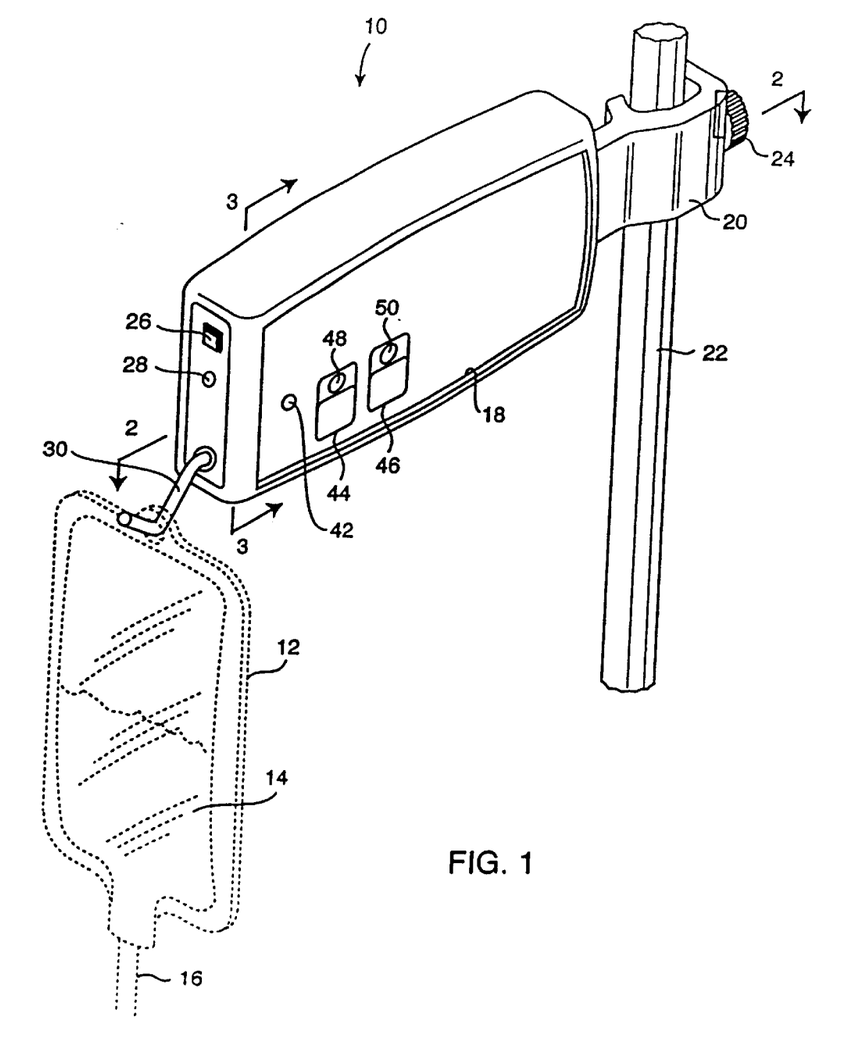
FIG. 1 is a perspective view of an infusion monitoring apparatus embodying the present invention attached to a vertical pole, and having a fluid bag in phantom hanging therefrom.
Figure 2:
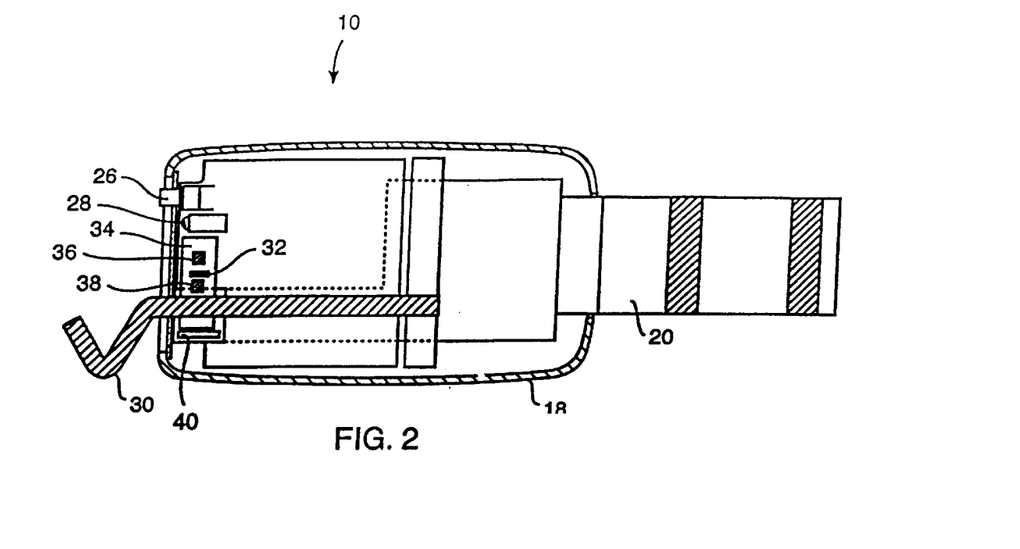
FIG. 2 is a side cross-sectional view taken generally along line 2—2 of FIG. 1.
Figure 3:
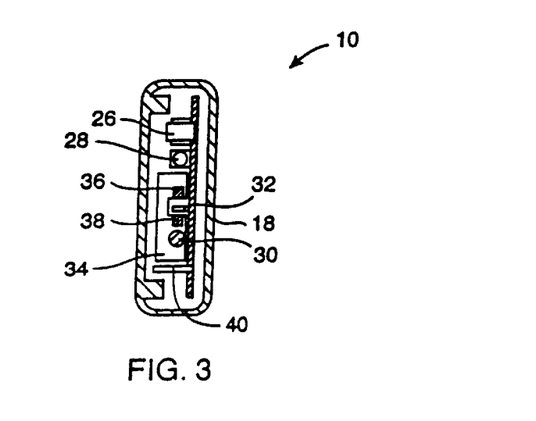
FIG. 3 is an end cross-sectional view taken generally along line 3—3 of FIG. 1.

With reference now to FIGS. 1–3, the apparatus 10 is comprised of a housing 18 having minimal crevasses and holes to allow for proper cleanliness in the surgery setting. A pole clamp 20 horizontally extends from one end of the housing 18 for connection to a vertical pole 22, as such vertical poles are commonly found in the hospital setting in the form of IV poles, or poles extending upwardly from a patient's bed. The pole clamp 20 includes a tightening knob 24 to secure the apparatus 10 to various diameter poles, typically 0.25 inch to 1.0 inch diameter poles. The apparatus 10 is long enough to extend away from the pole 22 so that the infusion bag 12 does not interfere with the pole 22, yet short enough not to extend farther than typical existing IV hooks. Typically, the apparatus 10 is approximately seven inches in length to fulfill these needs.

The apparatus 10 includes an alarm off switch 26 which will deactivate the audible alarm. The audible alarm is the primary alarm output of the invention, therefore, it's sound must be prominent enough to be heard "around the corner" in a typical ER setting. However, the invention contemplates producing an audible alarm which will not panic the patient, and can be set to distinctive types of sounds so as to not to be confused with other alarms, or various other alerts of the apparatus 10. If the alarm switch 26 is pressed prior to the alarm sounding, the audible alarm will be disabled for the near-empty condition current run only, however, the visual alarm 28 will remain functional. Typically, both the audible sound and visual alert will occur when the near empty weight is reached. The apparatus 10 is intended to detect the near empty weight of bags ranging in size from 50ml to 3 liters as such bags are typically used in the hospital. In order to activate the apparatus 10, a weight, such as a fluid bag 12, is hung from the hook of arm 30 which extends from the housing 18 generally opposite the pole clamp 20. The horizontally-oriented hook 30 is of a durable material and provides minimal movement, typically less than 0.050 inches, when a bag 12 is hung therefrom. Such an arm 30 can be comprised of 3/16 or 1/4 inch diameter aluminum rod, cut and bent to form a three inch straight portion internally and a hook end for hanging the fluid bag 12.

Within the housing 18, the arm 30 is associated with an electronic weight sensing mechanism or electronic position sensor, such as a transducer, load-cell, or Hall-Effect sensor. FIGS. 2 and 3 illustrate the preferred embodiment of the invention which incorporates a Hall-sensor 32. A machined metal block 34 is secured onto the arm 30 and holds two opposing magnets 36 and 38. The magnets 36 and 38 are approximately 1/8" diameter each, with the south poles facing each other so that a gap exists between the two magnets 36 and 38 with the Hall-sensor 32 disposed therebetween without physical contact. The result is that the arm 30 will bend slightly when weight is hung on the arm 30. The Hall-sensing device will then sense the distance between itself and the two opposing magnets as the block 34 is displaced and produce an output proportional to the two distances.

A mechanical stop 40 can be implemented to prevent excessive weight from bending the arm 30 and also to protect the Hall-sensor 32. The arm will typically hit the mechanical stop 40 if 1200 grams or more weight is hung from the arm 30. The mechanical stop 40 remains constant at 1200 grams. This allows operation of the bolus function with bags of 1 liter size or less. Larger bags, for example, a 3 liter bag will also flex the arm 30 to the stop 40. Until the weight is less than 1200 grams, the apparatus 10 cannot compute weights. Consequently, the bolus feature and the rate display feature are not operational with weights exceeding 1200 grams. The only significant change in the 1 liter mode versus infusion bags in excess of 1 liter being placed on the apparatus 10, is a higher weight range for programming the near empty set point.

The apparatus 10 is designed such that it sleeps most of the time to conserve power, yet is automatically activated when a weight, such as the fluid bag 12, is hung therefrom. The apparatus 10 operates from batteries, such as two "AA" batteries, for approximately six months. The apparatus 10 includes a low battery alarm 42, typically in the form of a LED visual alarm. During sleep, it awakes periodically to take weight measurements. If a weight exceeding a pre-programmed set point plus 50 grams is detected, the apparatus 10 goes into an active mode and begins weight processing to determine a near empty condition. The apparatus 10 stays active until the weight is below the predetermined empty point for more than ten minutes, or if the bag 12 is removed entirely. Typically, specific gravity of the solution is assumed to be 1.01 which approximates values for commonly used infusion solutions (e.g. normal saline, lactated ringers). The user is allowed to set the alarm trip weight by hanging a desired weight on the arm 30 and pressing and holding the alarm off button 26 for an excess of a predetermined time, such as three seconds. This new weight value, referred to as set point, will be recorded in non-volatile memory and can be reset at anytime. This feature allows healthcare personnel to preprogram the near empty set point by using a near empty infusion setup, or using weights.

A bolus feature is provided, typically for the one liter mode only, in which two bolus keys 44 and 46 for different bolus volumes, typically 250 and 500 ml. The term "bolus" herein is in reference to a preselected amount of fluid to be monitored. If a bolus key 44 or 46 is pressed, the current weight of the fluid bag 12 is recorded as the start point. The associated bolus light 48 or 50 will flash periodically to indicate a bolus measurement is in progress. Thus, if one thousand milliliters of fluid 14 is initially hung on the arm 30 of the apparatus 10, and the two hundred and fifty ml bolus button 44 pressed, once two hundred and fifty ml of fluid 14 have been infused, or lost from the bag 12, the alarm will sound. The bolus light 48 will typically be illuminated for approximately five seconds as a secondary alarm. The bolus key 44, 46 can only be activated if the remaining fluid weight is greater than the near empty set point weight plus the bolus weight, that is there must be fluid remaining in the bag which is in excess of the bolus selected. This feature can be utilized to the benefit of the medical care provider. The inventors are not aware of any previous devices incorporating such a bolus or intra-bag feature, which can be particularly useful in emergency rooms, obstetrical wards, and operating rooms.

The idea behind a fluid bolus is to administer a specified amount of fluid "wide open", that is, as fast as the intravenous line allows. Fluid boluses are commonly given in ER, OR and obstetric settings. Without such an alarm, "runaway" fluid bolus, where the bolus size greatly exceeds what was initially intended, is common. This problem is currently addressed in some settings by replacing gravity flow set-ups with infusion pumps, usually at considerable cost. Such pumps typically only deliver the fluid at less than one liter per hour, whereas use of the present invention will allow the full "wide-open" fluid flow at excess of six liters per hour. The difference in fluid flow can be life saving in certain circumstances. Another problem with infusion pumps is that they often alarm even when a slight interruption of flow is experienced. The monitoring apparatus 10 of the present invention can be programmed to ignore such interruptions of flow if they are only temporary in nature. It is also contemplated that the monitoring apparatus 10 include a display, or electronically interfaced with the display, to convert the sensing change of weight information to a rate of infusion.

The apparatus 10 is typically activated in the one liter mode. If apparatus 10 is to be used primarily with fluid bags in excess of 1 liter, such as 3 liter bags, the apparatus 10 can be programmed to accommodate such bags by replacing a battery while holding the 500 ml bolus button 46. This allows higher set point weight programming and disables the bolus function. Users can change back to the one liter mode by holding the 250 ml bolus button 44 while replacing a previously removed battery.

The apparatus 10 includes the following electronic components and features. A step-up voltage converter increases the voltage from the batteries to five volts internally. The converter draws minimal current as it operates constantly. A microcontroller having at least two thousand words of code space, non-volatile memory in the form of EEPROM, a ten bit on-chip A/D converter and multiple digital I/O pins are used to program the apparatus 10 and in conjunction with the Hall-effect sensor determine the weight loss from the fluid bag 12. A six bit digital-to-analog audio output circuit drives a 17 mm or 22 mm piezo with approximately five volts. A ceramic resonator time-base is used to provide repeatable timing and audible tones.

Figure 4:
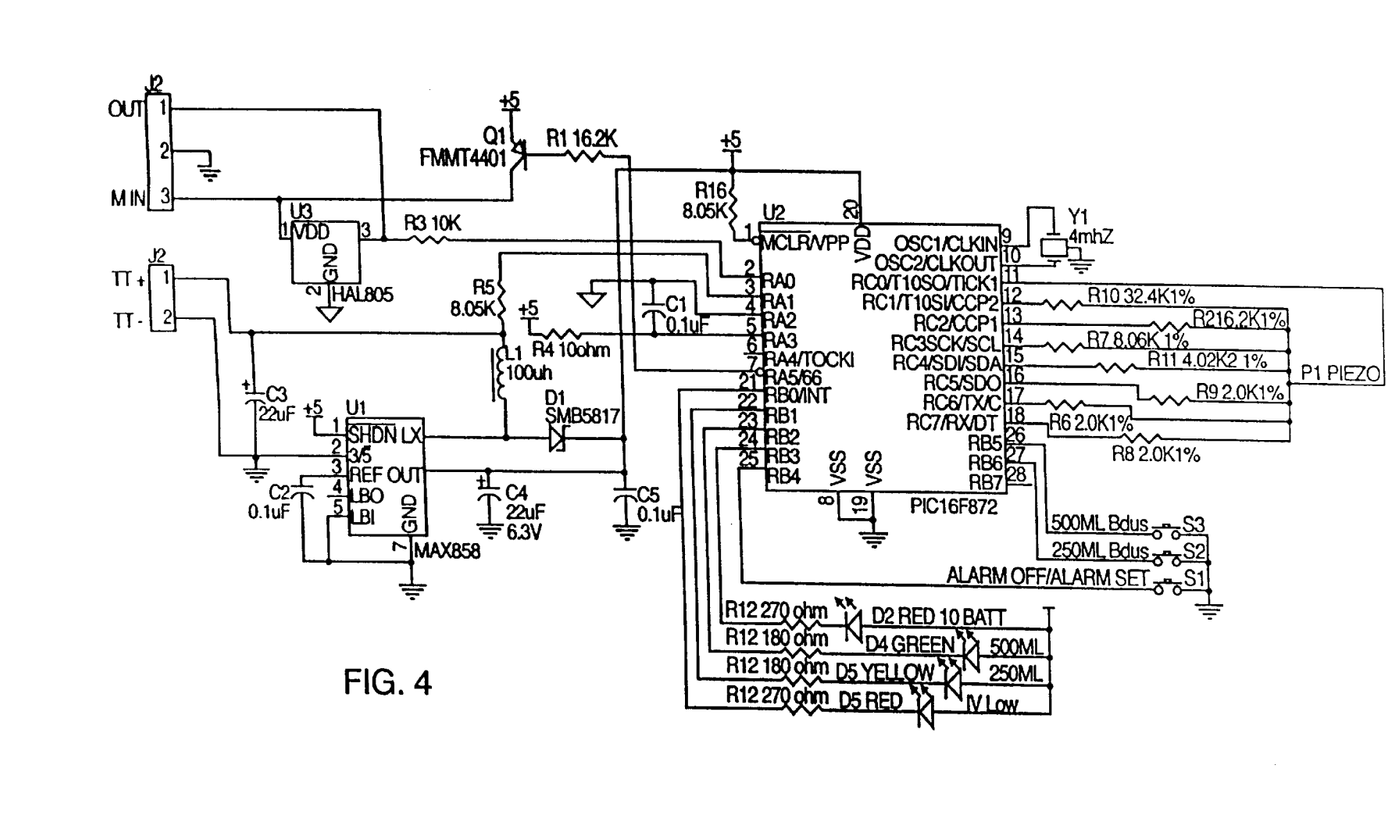
FIG. 4 is a schematic diagram used in accordance with the present invention.

With reference to FIG. 4, circuitry of the apparatus 10 in accordance with the present invention is provided in detail. According to the electronic schematic, regulator U1 comprises a MAX858 125 ma switching regulator. Microcontroller U2 comprises a PIC16F872-I/SO chip or suitable replacement. Sensor U3 comprises a HAL805 linear progressive Hall-sensor. Transistor Q1 comprises a FMMT4403

PNP transistor. Diodes D1 and D6 comprise SMB5817 Schotky diode of 1 amp. Diodes D2 and D3 comprise red LEDS, and diode D4 comprises a green LED while diode D5 comprises a yellow LED. Component Y1 comprises a 4 Mhz ceramic resonator. Component S1 comprises a TL1105JAF160Q 6 mm tact switch, while switches S2 and S3 comprise TL3301NF160QG/TR 6 mm tact switches. Component L1 comprises a 1812-104 J 100 uh 158 ma choke. Components Cx comprise 3300 pf 50V ceramic capacitors. Capacitors C1, C2, C5 comprise 0.1 ufd 16 volt ceramic capacitors. Capacitors C3, C4 comprise 22 ufd 6.3 v tantalum capacitors. Resistor R4 comprises a 10 ohm 5% 1/16 W resistor. Resistors R14, R15 comprise 180 ohm 5% 1/16 W resistors. Resistors R12, R13 comprise 270 ohm 5% 1/16 W resistors. Resistor R8 comprises a 4999 1% 1/16 W resistor. Resistor R6 comprises a 1.0K 1% 1/16 W resistor. Resistor R9 comprises a 2.0K 1% 1/16 W resistor. Resistor R11 comprises a 4.02K ohm 1% 1/16 W resistor. Resistors R3, R5, R7, and R16 comprise an 8.06K 1% 1/16 W resistor each. Resistors R1 and R2 each comprise a 16.2K 1% 1/16 W resistor. Resistor R10 comprises a 32.4K 1% 1/16 W resistor. Component P1 comprises a PT2726P 25 mm 2.5 khz piezo. Those skilled in the art will appreciate the interconnection of these components as illustrated in FIG. 4.

It should be understood by the reader that other possible weight sensing mechanisms and methods might be used. For example, a linear potentiometer which tracks the electrical resistance changes proportional to the distance of movement of a hangar bar. Moreover, the same movement might be sensed by use of an optical system where the output is proportional to the movement. Or, alternatively, an electro-magnetic system can be used where an inductor is excited by a frequency. When the hangar bar moves slightly from the weight, the metal interferes with the magnetic field around the indicator and modifies the frequency. The frequency then varies in direct proportion to the weight. It should also be noted that the Hall-effect device may also have a digital-proportional duty cycle output, instead of a voltage output. This would eliminate the need for an A/D converter. Yet another option is to use only one magnet instead of the two opposed magnets, although the output would be non-linear.

Figure 5:
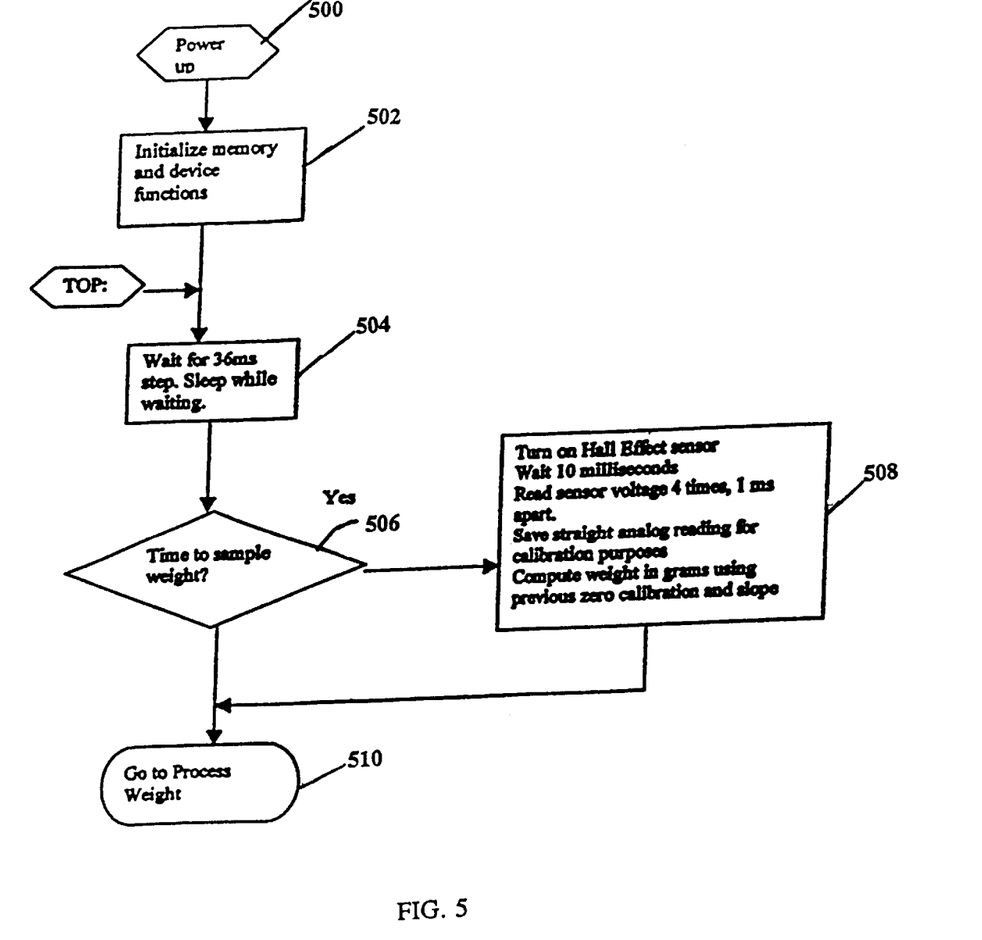
FIG. 5 is a flow chart of the steps taken in the initialization and sleep mode in accordance with the present invention.

With reference now to FIG. 5, the system sleeps between watch dog wake-up processes. The system periodically powers up (500) and initializes memory and device functions (502). The timing calibration is performed by staying awake and powered on 36 ms while counting the actual elapsed time using the internal counter. The true watch-dog period will then be computed. The system as a whole remains inactive, or asleep while waiting for the 36 ms (504). In the inactive state, that is no bag or weight on the arm 30, the system shuts off all LEDS and audio output. The system powers on the Hall-effect sensor every two seconds to sample the weight, in both the active and inactive states. The main loop of powering-up, processing weight, processing keys, and processing audio which is illustrated in FIGS. 5–10, is performed every watch-dog wake-up cycle. Once the loop finishes executing the called functions, the system is put to sleep until the watch-dog timer wakes it up again, approximately every 36 ms.

Once a weight that exceeds the set point weight plus a predetermined amount of weight, typically 50 grams, is detected on the arm 30, the system activates itself. At this time, the visual alarm LED 28 illuminates for two seconds to acknowledge start-up. The software then determines that it is time to sample the weight (506), at which point the Hall-effect sensor is powered on. Ten milliseconds are provided to fully power the Hall-effect sensor. The sensor voltage readings are performed four times, one millisecond apart. The software uses a 10 bit A/D converter to perform an analog read. The straight analog reading is saved for calibration purposes, but an average of the multiple readings is taken to help reject electrical noise, in the event that the apparatus 10 has been jostled. The software then computes the weight in grams using previous calibration and slope (508). The Hall-effect device shall be shut off again until the next reading at which point the software goes to the process weight flow chart (510) which is illustrated in FIGS. 6 and 7.

Figure 6:
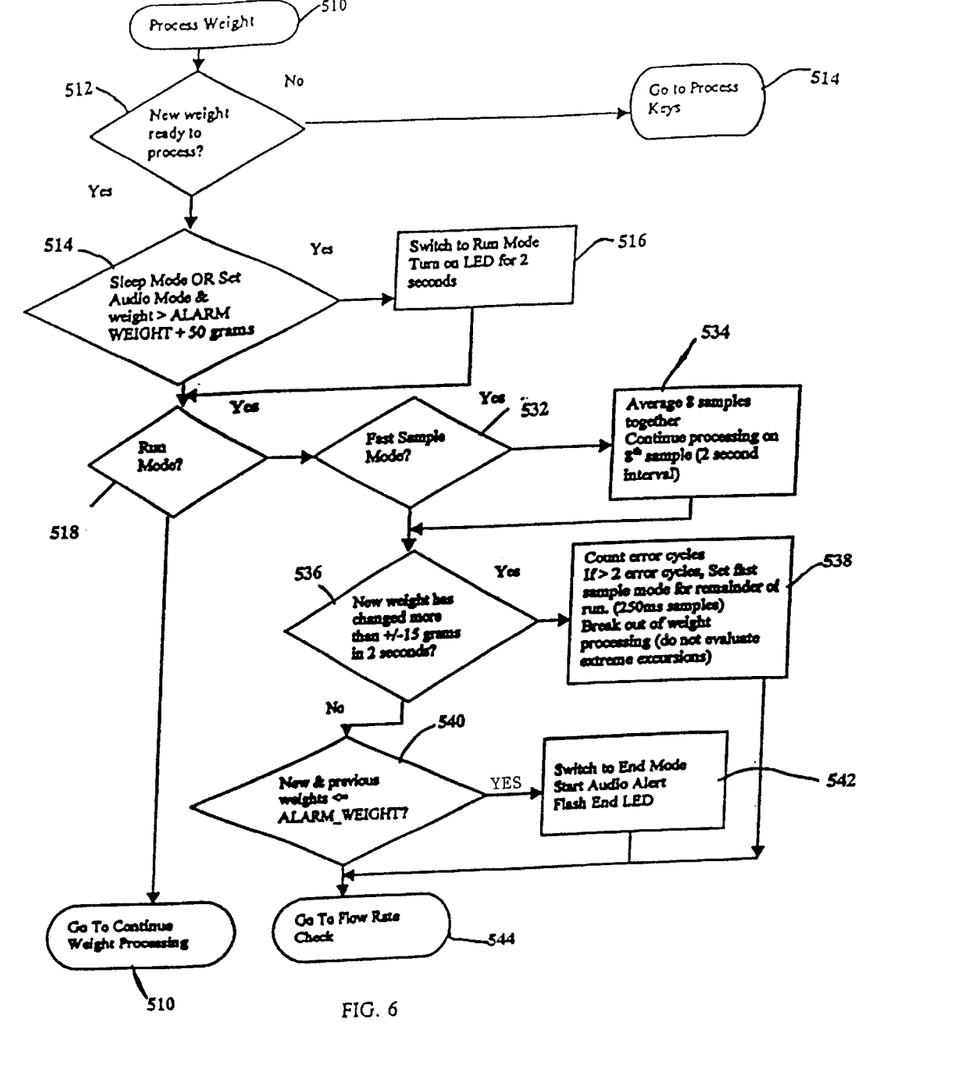
FIGS. 6 AND 7 are flow charts illustrating the steps taken during weight processing in accordance with the present invention.
Figure 7:
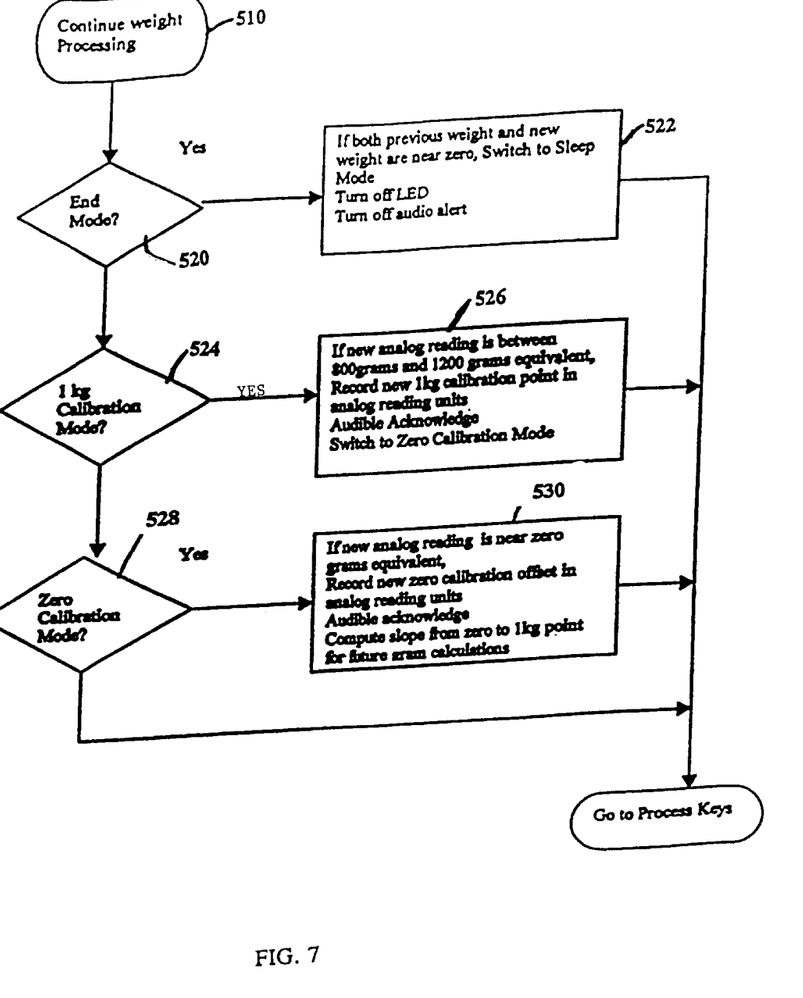

With reference now to FIGS. 6 and 7, if the new weight is not ready to be processed (512), the software goes to the process keys (514) sequenced to determine if any keys have been pressed. If the new weight is ready to be processed, the software determines if it is in sleep mode or set audio mode and the weight is greater than the set point plus 50 grams (514). If the software determines that it should be in the run mode instead of the sleep mode, it switches to the run mode and turns on the appropriate LED for approximately two seconds (516). If it is not to be in the run mode (518), a determination is made whether the mode should end (520). Thus, during a watch-dog wake-up cycle, without any weight hung from the arm 30, if both the previous weight and new weight are near zero, the apparatus 10 is switched to sleep mode and all LEDS and audio alerts are turned off (522).

However, if the system determines that it is in the one kilogram calibration mode (524) by producing a new analog reading between 800 grams and 1200 grams, with the proper switch depressed for more than three seconds, a new 1 kilogram calibration point is saved, an audible acknowledgment is made, and the system switches to zero calibration mode (526).

However, if the system determines that it is instead in a zero calibration mode (528), the new analog reading near zero grams is recorded as a new zero calibration, an audible acknowledgment is made, and a new slope is computed from zero to the 1 kilogram point for future calibrations (530).

Referring back to FIG. 6, if the weight exceeding the set point is still on the arm 30, the system determines whether to enter a fast sample mode (532). During 2 second intervals, multiple samples are taken and processed (534). The new reading is compared with previous readings to determine if the new reading is acceptable or out of range. If the new weight reading has changed more than 15 grams within 2 seconds (536), a fast sample mode is set for the remainder of the run. That is, the previous reading is not evaluated for bolus or empty comparisons. However, it is stored so it can be compared with the next reading for range. This allows a sudden weight shift caused by a bag being removed to be properly handled. The fast sample, or long-average mode, obtains a new weight reading approximately every 250 ms (538). This function shall add these readings together and compute the average value at the end of each 2 second period. The resultant value will then be processed as normal new weight reading. The system then determines whether the new and previous weight calculations are less than or equal to the predetermined alarm weight (540). If it has, the system switches to an end mode and begins the audio alarm alert, as well as flashing the appropriate LED (542). Of course, if the new and previous weights are not less than or equal to the alarm weight, the cycle continues until the newly calculated weight equals or falls below the alarm weight. The target weight is either the programmed set point weight, or the weight calculation for the bolus selected by depressing the appropriate switch.

Figure 8:
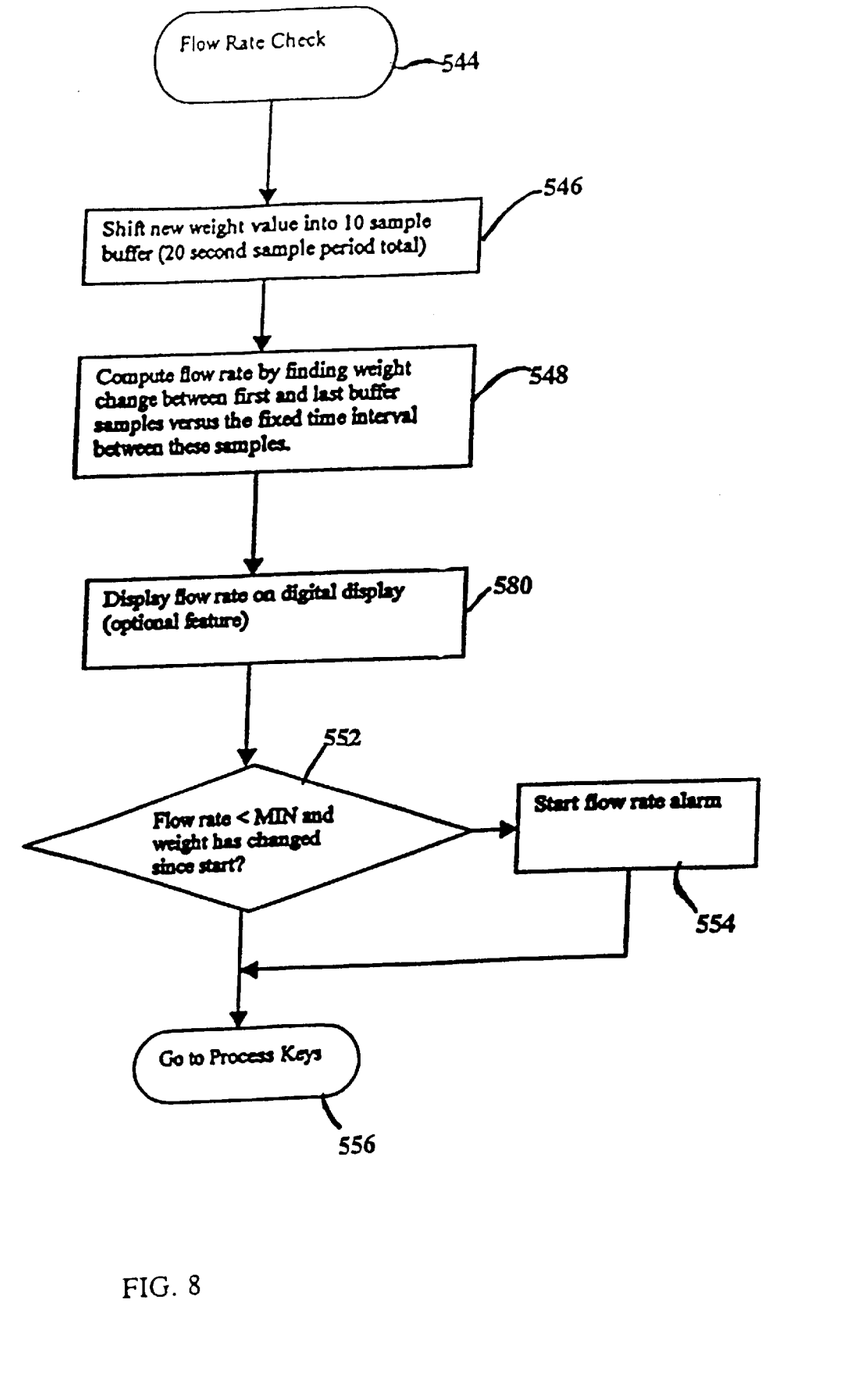
FIG. 8 is a flow chart illustrating the steps taken during rate flow check in accordance with the present invention.

With reference now to FIG. 8, a fluid infusion flow rate can be determined and checked (544) based upon the weight changes over time which were previously processed and calculated. A new weight value is shifted into ten sample buffers (546). The flow rate is computed by finding the weight change between the first and last buffer samples verses the fixed time interval between the samples (548). The flow rate is displayed on a digital display (550) either on the apparatus 10 itself, or another display. If the flow rate is determined to be less than the minimum and the weight has changed since the start of the process (552), a flow rate alarm is actuated (554). This would alert the medical personnel that the flow rate is not being accurately computed, or that there is a problem with the fluid delivery system.

Figure 9:
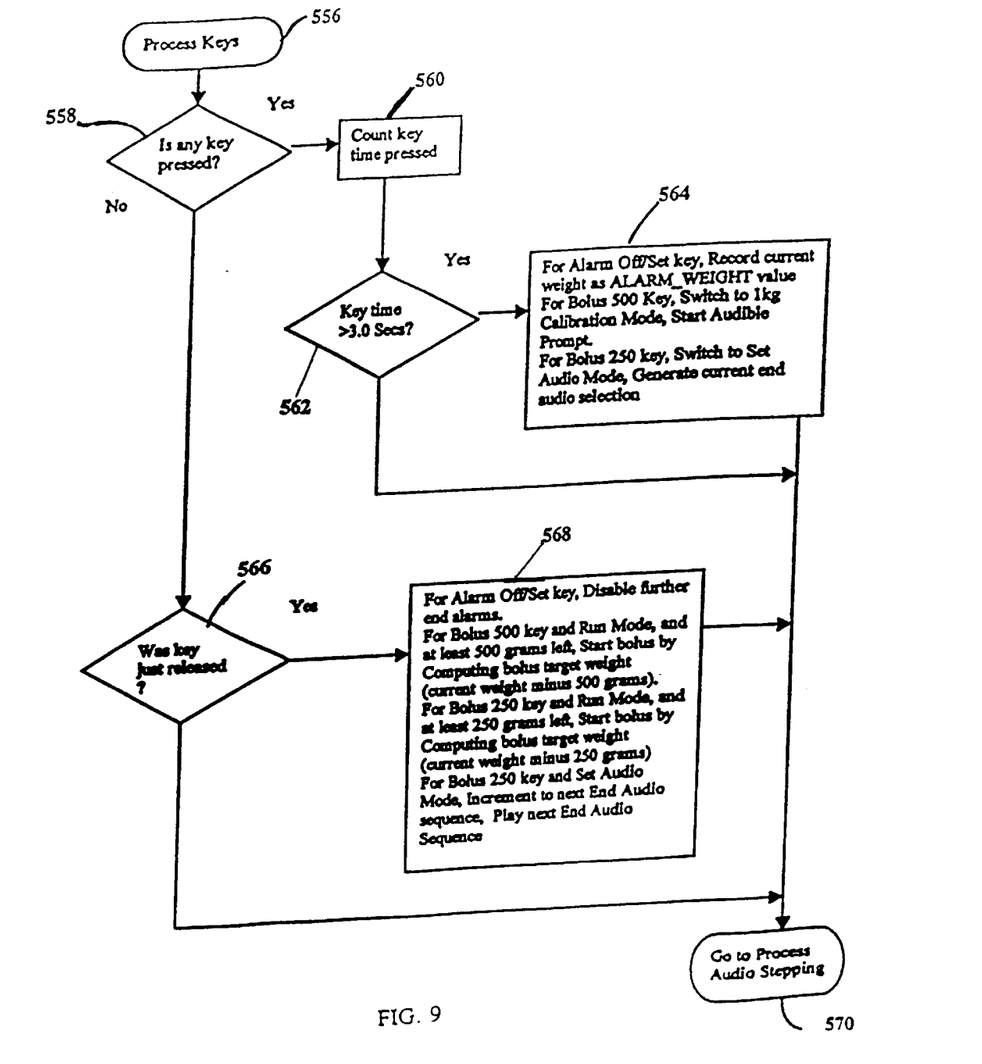
FIG. 9 is a flow chart illustrating the steps taken during key processing in accordance with the present invention.

Referring now to FIG. 9, the three key inputs are read approximately every 72 ms. These track any various key functions or activations such as alarm off, alarm set, bolus start, and calibrate, as described above. The process key sequence (556) begins by determining whether any key has been pressed (558). If a key has been pressed, the amount of time that the key is pressed is counted (560). If the 250 milliliter bolus key is pressed for more than three seconds (562), the apparatus enters into audio select mode. In this mode, the user can cycle through a selection of audio tones at two volume settings. If the 500 milliliter bolus key is pressed for more than three seconds (562), the apparatus enters into calibration mode and looks for a 1 kilogram calibration weight. After the 1 kilogram weight is acknowledged, the weight is removed and the system performs a zero calibration (564). If the key is merely pressed and released in less than 3 seconds (566), the system determines which key was pressed and which function to perform (568). For example, if the alarm off key has been depressed, further audible alarms are disabled. If the bolus 500 or 250 ml key has been depressed, the system tracks the appropriate bolus weight. The appropriate audio prompts are activated to alert the user of the apparatus 10 that the system has acknowledged their request.

Figure 10:
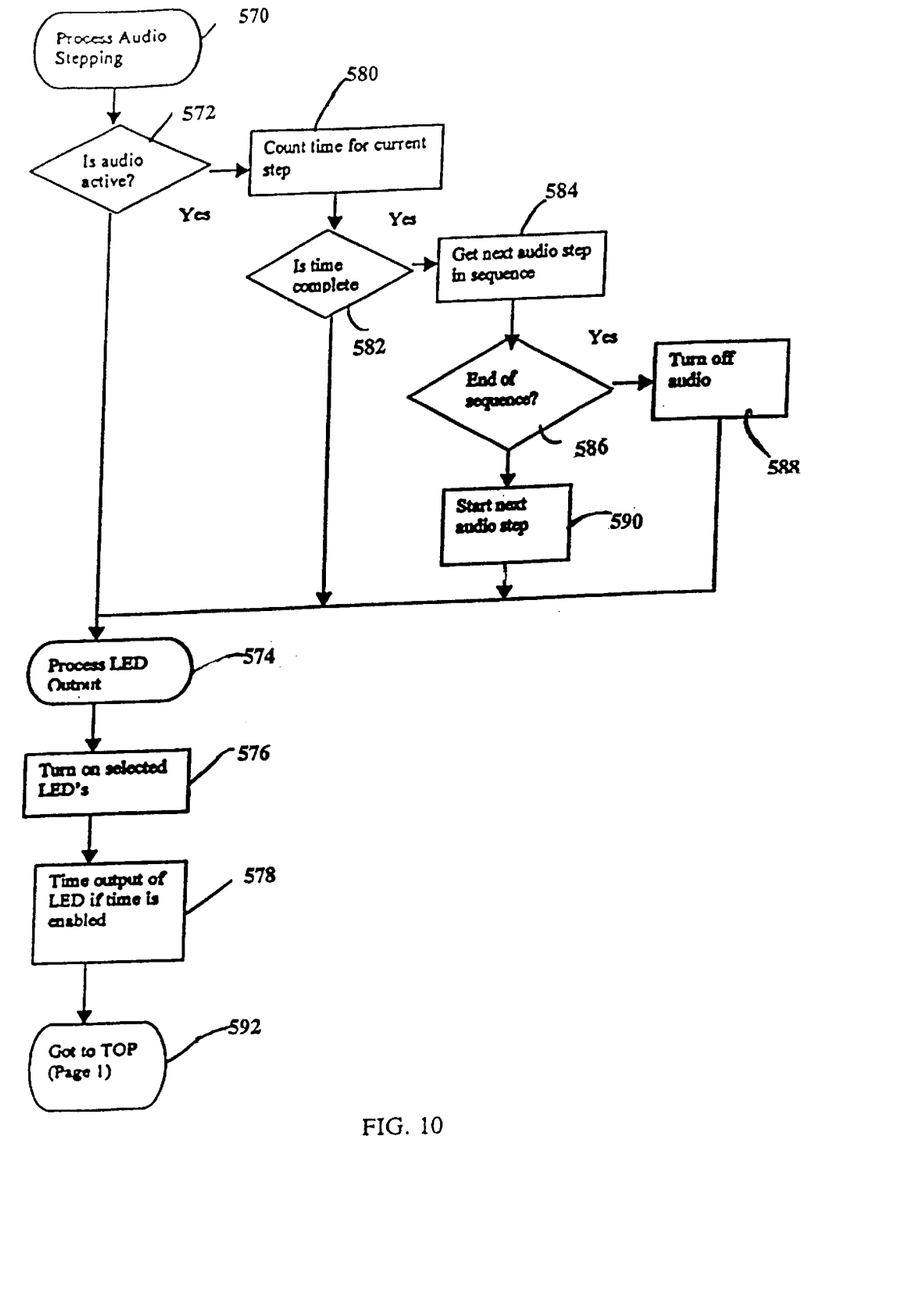
FIG. 10 is a flow chart illustrating the steps taken during audio processing in accordance with the present invention.

With reference now to FIG. 10, the audio function processes are comprised of three functions. The first function is called by other functions to start a specific audio sequence. Thus, during the process of audio stepping (570) it is first determined if the audio is active (572). As stated above, the audio may be inactivated by depressing the alarm off button 26. If the audio is inactive, the system relies upon processing the LED output (574) so that the appropriate LED is illuminated or flashed to alarm the user. Thus, instead of generating an audible alarm, the selected LED is turned on (576) when the alarm is activated. It should be understood by the reader that such LEDS are illuminated regardless of whether the audio is in the active or inactive state. Preferably, the LED will illuminate for a preset time period, and turn off after that time period, or if the fluid bag 12 is removed from arm 30 (578).

If the audio alarm is activated, a preset time is counted for the current step (580), and upon completion (582) the next audio step is obtained in the sequence (584). At the end of the sequence (586), the audio is turned off (588). If the sequence has not come to an end, the next audio step is begun (590). Thus, various pointers and sequence counters are initialized for stepping through the desired tone sequence that is stored in a table. Governing the audio sequences is a table within the software that includes codes for the software for each sequence desired. Different sound levels, and even audible tones can be selected so that the apparatus 10 can be customized to the particular hospital setting so as to not interfere with other alarms and the like.

Once the system has performed its activated watch-dog procedure, or the fluid 14 from the fluid bag 12 has been infused and the fluid bag 12 removed from arm 30, the system reenters its inactive state (592) and cycles through the process steps of sleeping and periodically activating until being activated by hanging a weight from arm 30. Periodically sleeping between steps significantly increases the battery life of the apparatus 10.

It is contemplated that a central display station using wireless technology could monitor multiple infusion monitoring apparatus' 10 simultaneously. Thus, a central display could be placed in nurse's station which would simultaneously monitor the fluid infusion of multiple patients in multiple rooms. Also, data could be transmitted from the apparatus 10 to a hand-held device, such as a pager, which could be worn by healthcare personnel and track one or more apparatuses 10.

The monitoring infusion apparatus 10 of the present invention provides many advantages over the prior art. The apparatus 10 is simple to use. In order to activate the apparatus 10, an infusion bag is merely placed on the arm 30 of the apparatus 10. The user does not have to look at the device or touch it until the bag hits the programmed near empty set point, at which point an alarm will sound audibly and visually. At that point the user can take the bag 12 off of the arm 30 which inactivates the alarms, or press the appropriate button to turn the alarm off. After the near empty bag 12 is removed, the apparatus 10 is ready for the next fluid bag 12. A 250 or 500 ml bolus can be rapidly infused into the patient and tracked accurately by activating the alarm as soon as the fluid bolus is completed. This enables the medical care provider to accurately dispense the required fluid or medication. Conversely, the 250 or 500 ml bolus functions can be used as intra-bag markers with any infusion rate. It is extremely difficult to generate a false alarm for either the near empty set point, or the bolus feature. The apparatus detects and filters aberrant weight measurements and can increase the frequency of sample cycling to minimize the occurrence of false alarms. Near empty and end-of-bolus conditions are accurately and reliably detected. The electronic sensor used in the present invention, as well as a microprocessor controlled circuitry, ensure that the calculations are consistent over time without mechanical failure as with prior art devices.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. An infusion monitoring apparatus, comprising:
   a housing;
   a pole clamp extending from the housing for removable attachment to a pole;
   an arm extending from the housing for holding an infusion fluid bag;
   an electronic weight sensing mechanism disposed within the housing and associated with the arm;
   a control circuit electronically connected to the sensing mechanism for detecting a no-fluid-flow condition and a preselected amount of fluid loss condition; and
   an alarm activated when the no-fluid-flow condition, or the preselected amount of fluid loss condition has been detected.

2. The infusion monitoring apparatus of claim 1, wherein the electronic weight sensing mechanism comprises a magnet associated with the arm, and a Hall-effect sensor disposed adjacent to the magnet.

3. The infusion monitoring apparatus of claim 1, wherein the electronic weight sensing mechanism comprises a load-cell associated with the arm.

4. The infusion monitoring apparatus of claim 1, including externally accessible switches on the housing for selecting an amount of fluid loss to be monitored.

5. The infusion monitoring apparatus of claim 1, including a low battery alarm.

6. The infusion monitoring apparatus of claim 1, wherein the arm extends horizontally from the housing generally opposite the pole clamp.

7. A process for monitoring fluid infusion into a patient, comprising the steps of:
hanging a fluid infusion bag from a monitoring apparatus;
periodically measuring the weight of the fluid infusion bag, using an electronic weight sensing mechanism and a control circuit, to detect a no-fluid-flow condition and a preselected amount of fluid loss condition; and
activating an alarm when the no fluid flow condition, or the preselected amount of fluid loss condition has been detected.

8. The process of claim 7, including the step of setting a near empty bag set point weight by hanging a weight from the monitoring apparatus, electronically saving the near empty bag set point weight, and using the near empty bag set point weight to detect the near empty bag condition.

9. The process of claim 8, wherein the near empty bag set point weight approximates an empty fluid infusion bag system with a nominal amount of fluid therein.

10. The process of claim 7, including the step of depressing a switch on the monitoring apparatus for selecting the monitoring of an amount of fluid to be infused totaling less than the fluid within the fluid infusion bag.

11. The process of claim 7, wherein the measuring step includes the step of taking multiple weight measurements over a short period of time and creating and electronically saving a reading.

12. The process of claim 11, including the step of determining if the reading is within acceptable limits when compared to prior electronically saved readings.

13. The process of claim 12, including the step of accepting a reading within acceptable limits, or taking additional weight measurements over a short period of time to create a new reading if the immediately prior reading was without the acceptable limits.

14. The process of claim 7, wherein the no-fluid-flow condition is detected by determining that the weight of the fluid infusion bag has not decreased over a predetermined period of time.

15. The process of claim 7, wherein the no-fluid-flow condition is detected by determining that the weight of the fluid infusion bag has not decreased a predetermined amount over a period of time.

16. The process of claim 7, including the step of calculating and displaying the rate of fluid loss from the fluid bag.

17. The process of claim 7, including the step of maintaining the monitoring apparatus in a semi-inactive, battery conserving state and periodically self-activating to determine if a weight has been hung from the monitoring apparatus.

18. The process of claim 7, including the step of activating an alarm when low battery power is detected.

19. The process of claim 7, including the step of transmitting a signal to a remote electronic device to activate an alarm when the no fluid flow condition or the preselected amount of fluid loss condition has been detected.

20. An infusion monitoring apparatus, comprising:
a housing;
a pole clamp extending from the housing for removable attachment to a pole;
an arm extending from the housing for holding an infusion fluid bag;
an electronic weight sensing mechanism comprising a magnet associated with the arm, and a Hall-effect sensor disposed adjacent to the magnet;
a control circuit electronically connected to the sensing mechanism for detecting at least one of (1) a no-fluid-flow condition, (2) a near empty bag condition, and (3) preselected amount of fluid loss condition; and
an alarm activated when (1) the no-fluid-flow condition, (2) the near empty bag condition, or (3) the preselected amount of fluid loss condition has been detected.

21. An infusion monitoring apparatus, comprising:
a housing;
a pole clamp extending from the housing for removable attachment to a pole;
an arm extending from the housing for holding an infusion fluid bag;
an electronic weight sensing mechanism comprising a load-cell disposed within the housing and associated with the arm;
a control circuit electronically connected to the sensing mechanism for detecting at least one of (1) a no-fluid-flow condition, (2) a near empty bag condition, and (3) preselected amount of fluid loss condition; and
an alarm activated when (1) the no-fluid-flow condition, (2) the near empty bag condition, or (3) the preselected amount of fluid loss condition has been detected.

22. An infusion monitoring apparatus, comprising:
a housing;
a pole clamp extending from the housing for removable attachment to a pole;
an arm extending from the housing for holding an infusion fluid bag;
an electronic weight sensing mechanism disposed within the housing and associated with the arm;
a control circuit electronically connected to the sensing mechanism for detecting at least one of (1) a no-fluid-flow condition, (2) a near empty bag condition, and (3) preselected amount of fluid loss condition;
externally accessible switches on the housing for selecting an amount of fluid loss to be monitored; and
an alarm activated when (1) the no-fluid-flow condition, (2) the near empty bag condition, or (3) the preselected amount of fluid loss condition has been detected.

23. A process for monitoring fluid infusion into a patient, comprising the steps of:
hanging a fluid infusion bag from a monitoring apparatus;
periodically measuring the weight of the fluid infusion bag, using an electronic weight sensing mechanism and a control circuit, to detect at least one of (1) a no-fluid-flow condition, (2) a near empty bag condition, and (3) a preselected amount of fluid loss condition;
depressing a switch on the monitoring apparatus for selecting the monitoring of an amount of fluid to be infused totaling less than the fluid within the fluid infusion bag; and
activating an alarm when (1) the no fluid flow condition, (2) the near empty bag condition, or (3) the preselected amount of fluid loss condition has been detected.

24. A process for monitoring fluid infusion into a patient, comprising the steps of:
- hanging a fluid infusion bag from a monitoring apparatus;
- periodically measuring the weight of the fluid infusion bag, using an electronic weight sensing mechanism and a control circuit, to detect at least one of (1) a no-fluid-flow condition, (2) a near empty bag condition, and (3) a preselected amount of fluid loss condition; and
- activating an alarm when (1) the no fluid flow condition, (2) the near empty bag condition, or (3) the preselected amount of fluid loss condition has been detected;
- wherein (1) the no-fluid-flow condition is detected by determining that the weight of the fluid infusion bag has not decreased over a predetermined period of time.

25. A process for monitoring fluid infusion into a patient, comprising the steps of:
- hanging a fluid infusion bag from a monitoring apparatus;
- periodically measuring the weight of the fluid infusion bag, using an electronic weight sensing mechanism and a control circuit, to detect at least one of (1) a no-fluid-flow condition, (2) a near empty bag condition, and (3) a preselected amount of fluid loss condition; and
- activating an alarm when (1) the no fluid flow condition, (2) the near empty bag condition, or (3) the preselected amount of fluid loss condition has been detected;
- wherein (1) the no-fluid-flow condition is detected by determining that the weight of the fluid infusion bag has not decreased a predetermined amount over a period of time.

26. A process for monitoring fluid infusion into a patient, comprising the steps of:
- maintaining the monitoring apparatus in a semi-inactive, battery conserving state and periodically self-activating to determine if a weight has been hung from the monitoring apparatus;
- hanging a fluid infusion bag from a monitoring apparatus;
- periodically measuring the weight of the fluid infusion bag, using an electronic weight sensing mechanism and a control circuit, to detect at least one of (1) a no-fluid-flow condition, (2) a near empty bag condition, and (3) a preselected amount of fluid loss condition; and
- activating an alarm when (1) the no fluid flow condition, (2) the near empty bag condition, or (3) the preselected amount of fluid loss condition has been detected.

\* \* \* \* \*